United States Patent [19]

Downey

[11] Patent Number: 4,861,155
[45] Date of Patent: Aug. 29, 1989

[54] METHOD AND APPARATUS FOR MEASURING CURVATURE OF THE CORNEA

[76] Inventor: Max Downey, 904 Greensburg St., Columbia, Ky. 42728

[21] Appl. No.: 188,709

[22] Filed: May 4, 1988

Related U.S. Application Data

[63] Continuation-in-part of Ser. No. 929,483, Nov. 12, 1986, abandoned.

[51] Int. Cl.$^4$ .......................... A61B 3/10; A61F 17/32
[52] U.S. Cl. ..................................... 351/212; 128/305
[58] Field of Search ............................. 351/212, 219; 128/303.1, 305, 639, 660, 649; 33/507

[56] References Cited

U.S. PATENT DOCUMENTS 4,212,107  7/1980  Mezzasalma ........................ 33/507
4,665,914  5/1987  Tanne ................................. 128/305

Primary Examiner—Bruce Y. Arnold
Assistant Examiner—P. M. Dzierzynski
Attorney, Agent, or Firm—Lloyd M. Forster

[57] ABSTRACT

Method and apparatus for measuring corneal curvature through mechanical measurement of longitudinal probe positioning in contacting the surface of the subject's cornea at predetermined radial and angular positions relative to the central apex of the eye. Electrical sensing of the cornea surface by contact with a conductive probe is employed to generate an audible signal with accurate encoder means for registration of probe axial position. Both manually actuated and automatic embodiments are disclosed each involving apparatus mounted on a solid base including a head rest for the patient and an objective for eye fixation during the examination.

8 Claims, 6 Drawing Sheets

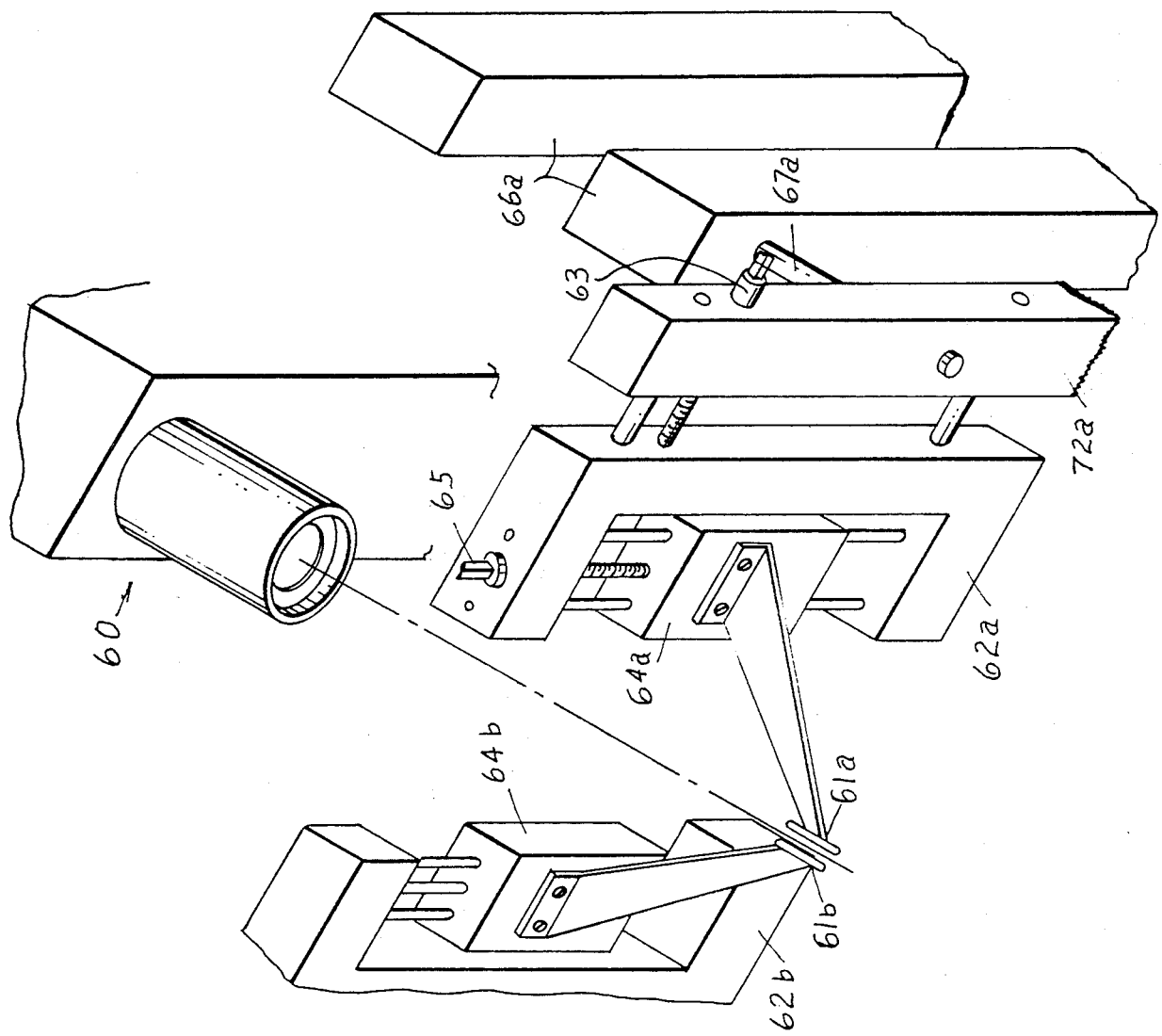

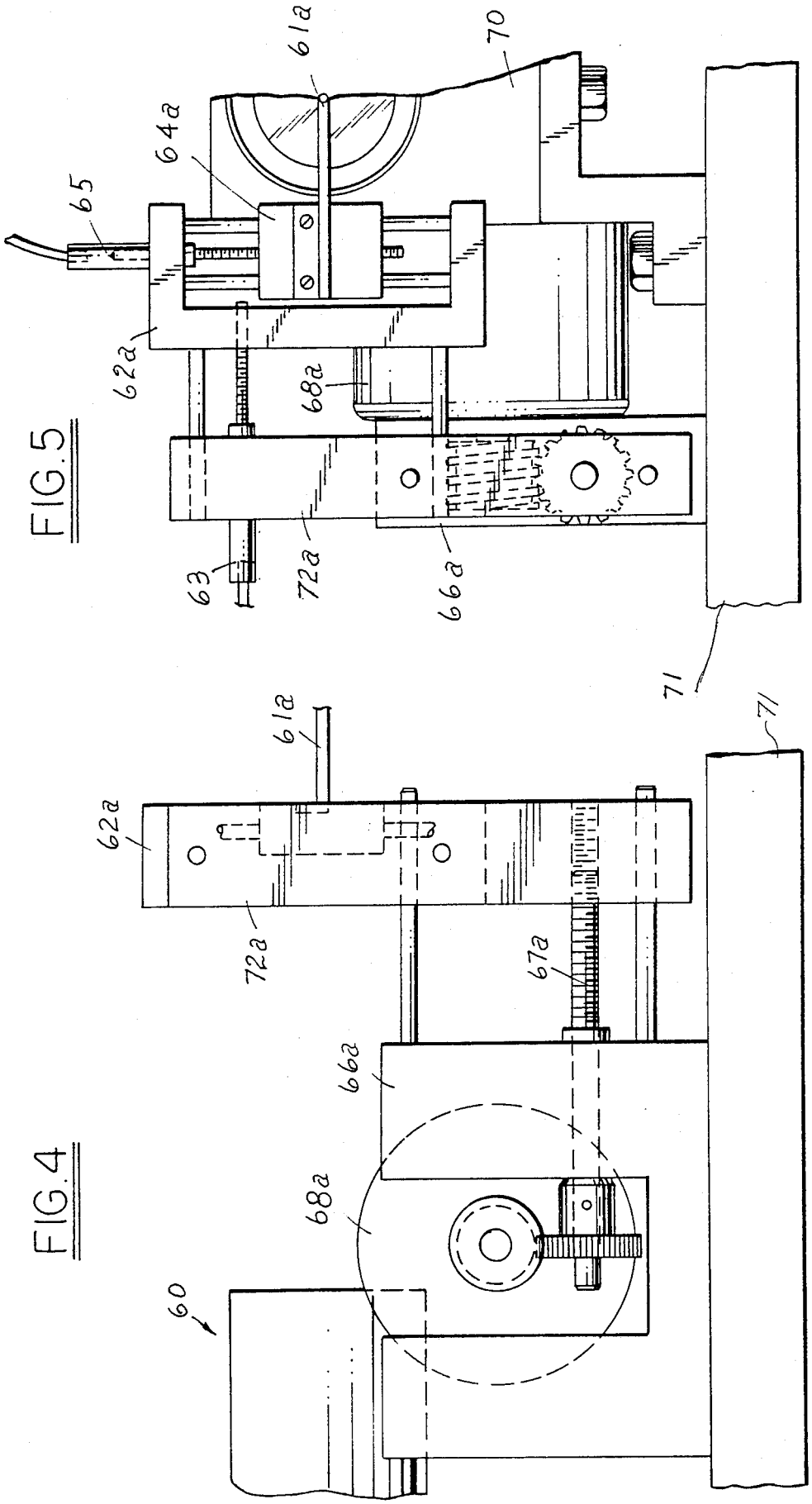

METHOD AND APPARATUS FOR MEASURING CURVATURE OF THE CORNEA

This application is a continuation-in-part of copending application, Ser. No. 06/929,483 filed on Nov. 12, 1986 now abandoned.

BACKGROUND OF THE INVENTION

Conventional apparatus and method for measuring curvature of the cornea employing Keratometer or Ophthalmometer are disclosed in a published Bausch and Lomb Keratometer Instruction Manual. The basic principal is optical measurement of corneal curvature of the eye along two principal meridians through use of a Keratometer which consists essentially of a target which is imaged by the cornea, and a telescope to observe this image. Measurement of the target image reveals the corneal curvature in diopters with the variations in curvature, (astigmatism). Operator focusing of the instrument will clarify images of the target mire of the patient's eye. Measuring the horizontal or near horizontal meridians, measuring the vertical or near vertical meridians, and determining the difference between the two measurements indicates the amount of corneal astigmatism. A scale for each of the horizontal and vertical meridians on the instrument indicates the actual diopter power of the cornea in each meridian. With the Keratometer in proper adjustment, a zone approximately 3.0 mm in diameter is measured. When the instrument is properly centered on the cornea the patient looks directly in through the center of the target. There is an aperture in the target center through which the patient sees an image of his own eye. This definite fixation holds the patient's eye centered while observations are made by the operator.

In the case of lens measuring method and apparatus, as distinguished from human cornea, mechanical and electrically conductive means have been employed to measure curvature, for example by measuring the relative positioning of a conductive ring for supporting a lens in either convex or concave orientation while a central movable probe is raised to a point touching the lens as signaled by establishing an electrical circuit. U.S. Patent 4,212,107 discloses such method and apparatus.

U.S. Pat. No. 4,665,914 discloses an instrument for automating radial keratotomy and other corneal operations which includes one or more probe sensors with extendable tips which, by measuring electrical resistivity, are responsive to contact occurring with the corneal surface. Positioning of the probe sensor(s) over various points of the corneal surface provides data signals which enable the surface topography of the cornea to be mapped by a micro-processor. The probe sensor(s) are used with a ring-like fixture attachable by vacuum to the eye and comprised of a fixed outer ring and a movable inner ring, the fixture providing mounting and/or support for these elements while permitting movement to different meridial locations by rotation of the inner ring. One arch element bridging the diameter of the ring fixture supports the probe sensor(s). In a modification, small motors, controlled by the microprocessor, drive the probe sensor(s) in their respective movement over the corneal surface.

SUMMARY OF THE INVENTION

Applicant's method and apparatus for measuring corneal curvature employs the electrical resistance from the surface of the patient's cornea to his chin to detect contact of an electrically conductive probe that, when applied to the eye will complete a circuit which is adapted to provide an audible tone indicating the cornea has been touched. Anesthetizing of the eye renders it insensitive to the probe contact involved. The system has a manual component as well as two electronic components and an optical component. Apparatus is housed with means that will allow the operator using the manual component while being viewed through the optical component to know precisely the moment he makes contact with the surface of the cornea through an audio tone supplied through a first electronic component. The second electronic component in the system enables the operator to know to the 1/100 millimeter how far the mobile probe has traveled inward from a tangent parallel to the corneal apex. This distance is then converted mathematically to the dioptric value of the corneal curve being measured. While some inaccuracy is inherent incident to the subject's eye movement during examination, e.g. slight pulsation responsive to heartbeat, the exactness of physical measurement of probe positioning and axial displacement vastly minimizes any error and increases the area of curvature under examination as compared to optical methods currently in use.

The optical component provides necessary magnification to the observer of the area being studied with means for adjusting the ocular to provide exact focus to any operator's eye which may have varying degrees of amotropia. Manual operation of the measuring device is refined down to the movement of a cylinder until an audio tone is heard. The device is equipped with modes designed to measure specific areas of the cornea which the operator selects by rotating a "mode selector" which, in a specific embodiment, provides eight cardinal positions and other radials as desired by the observer available for measurement at equally spaced angular intervals. The mobile probe is designed to have lateral selection modes from 1 to 10 millimeters away from the center area of the focus, and by using an alternate probe, the slope at the limbus can be measured. By choosing the desired setting one can then measure ten separate positions each with one millimeter separation along eight angularly separate radials with an electric detector that, when applied to the eye, will complete the circuit of the audible tone indicating the cornea has been touched. The audible tone is achieved by measuring the distance in ohms from the subject's eye being position to the subject's chin being negative to complete a circuit. This in turn is relayed to another electrical circuit that is sufficient to provide the audible tone.

An optical shaft encoder or equivalent potentiometer is mounted on the device to transmit a digital signal to be counted. The proportionate ratio of movement of shaft encoder revolution to distance of mobile probe movement is one revolution per one millimeter of movement. The digital signal provided by the encoder is displayed by an LED counter in millimeters and the chord of the cornea is then converted to dioptic slope value mathematically.

The method and apparatus provided a potential for a complete contour "map" of the cornea with depth points relative to the apex at any ten points with one millimeter spacing along an arc extending toward the center apex of focus for each of eight equally spaced intervals with 45° separation. It is of course unnecessary to measure every potential point on the cornea and the number and spacing of the measurements may be selectively chosen by the operator to meet the specific needs of the patient involved.

A single probe is employed and with the patient's eye fixed in an examining position where the reflection of his eye will provide an image of the mire in the center of his pupil, as in the case of a Keratometer. A "0" tangent plane of the apex at the center of the cornea is established by optical focus with all probe readings establishing depth relative thereto based on the angular setting and radial distance of readings on either side of the apex. Accurate differential depth values are established which are translated into corneal curvature in diopters.

In a new modification of the foregoing manual operation, the single probe is replaced with automated operation of two probes. A central monitoring device, through closed circuit T.V., enables the practitioner to view the complete eye while measurements are being made. Two probes operate separately. Four stepper motors are used to control the X,Y,Z-axes for plotting the topography of the cornea. The first motor controls the X-axis positioning of both probes simultaneously in equal increments. A second motor controls the Y-axis of both probes simultaneously in equal increments. The third motor controls one probe and the fourth motor the other probe, each along the Z-axis, but independently until corneal contact is sensed by separate electrical resistance circuits.

All the separate motors are controlled by a commercially available stepper motor controller under a computer control which runs the program for selection of data points by instructions to the motors. The controller reads back the position of the motors once each resistance circuit is completed between the probe touching the eye and the patient's chin in the chin rest. The distance moved is calculated from a known reference point and this distance from the first probe along with data returned in like manner from the second probe, is mathematically converted on an arc value determined by the position of the X-axis setting of the respective probes. These settings can be a range of 0 to 15+ millimeters from apex of the cornea depending on the practitioner's selection during the initial patient profile programming phase.

Such phase is completed by the practitioner prior to any measurements being made. The computer's prompt must be answered within the instrument's ranges for a complete set of data retrieval. Once entered, the computer program and the controller completes the routine of selected data points requested, calculates the arc curve of each request and is capable of averaging multiple arcs for additional empirical information. Information is printed out as raw data or placed into graphics.

BRIEF DESCRIPTION OF THE DRAWINGS

FIG. 1 is a sectional side elevation of the mechanical and optical apparatus employed in the present invention shown on two sheets designated 1A and 1B;

FIG. 3 is a schematic perspective view of apparatus employed in the modified automated system;

FIG. 4 is a fragmentary side elevation of the apparatus employed in providing three axis movement of each of two probes;

FIG. 5 is an end view of the apparatus illustrated in FIG. 4;

Figure 1A:
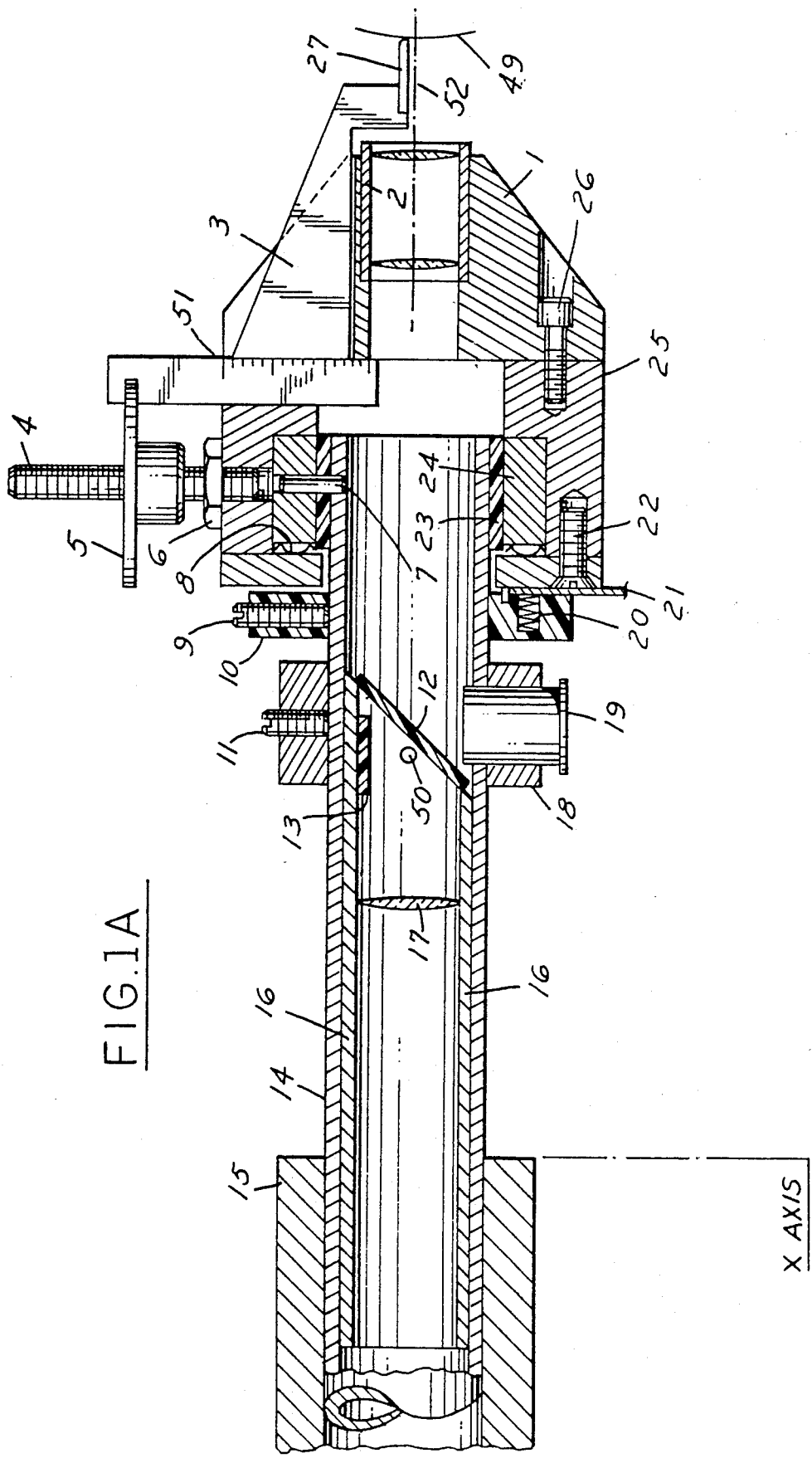
With reference to FIG. 1A, the components of the apparatus include lens holder 1, lens 2, adjustable contact probe mount 3, threaded rod 4, adjusting knob 5, lock nut 6, key pin 7, spring thrust washer 8, set screw 9, plastic insulating ring 10, set screw 11, optical plastic beam splitter 12, mirror 13, mobile casing 14, housing cap 15, lens holder 16, lens 17, retaining ring 18, light source 19, spring 20, electrical contact lead 21, flat head screws 22, plastic insulating ring 23, bushing 24, rotatable head 25, cap screw 26 and contact probe 27.
Figure 1B:
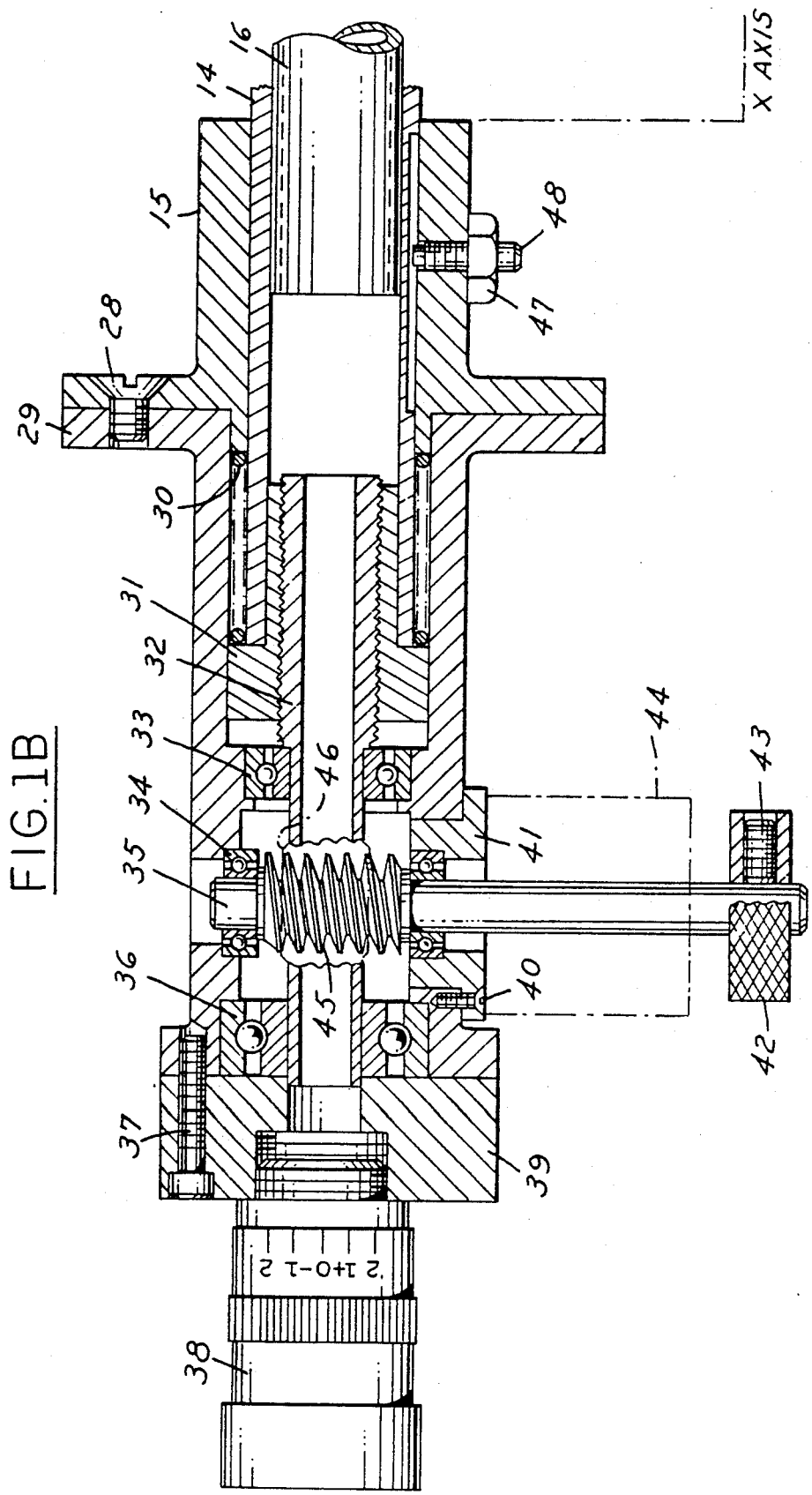
With reference to FIG. 1B, additional components of the apparatus include flathead screws 28, three required, housing 29, compression spring 30, nut 31, feed screw 32, bearing 33, bearing 34, two required, worm shaft 35, bearing 36, cap screw 37, three required, then times power ocular assembly 38, bearing cap 39, flat heads screw 40, three required, bearing cap 41, adjustment knob 42, set screw 43, encoder 44, worm gear 45, worm wheel 46, not shown, lock nut 47, and key screw 48.

In operation, the cornea of a patient's eye, schematically shown at 49 in a fixed position assisted by chin and headrest with the patient's eye focused on objective 50, is anesthesized and contacted by electrically conductive probe 27 which is radially adjusted by knob 5, angularly adjusted by rotation of head 25, and axially advanced by adjusting knob 42 until contact is made, sensed by electrically conductive circuit from probe 27 to conductor 21 which is completed through a lead to the patient's chin rest lowering a resistance adapted to produce an audible sound as hereinafter described.

Radial adjustment of probe 27 is indicated by a scale on slide 51 to which probe mount 3 is attached and which is displaced by rotation of adjustment knob 5, for example, one millimeter per revolution. Typically such adjustment may be made to provide as many as ten "readings" on a radial arc of the cornea displaced from one to ten millimeters from the apex at the center of the cornea of the patient's eye.

Once the apparatus is adjusted to the patient's eye level and centered, by mounting means not shown, and advanced to a proximity position of the probe 27, an initial contact at the one millimeter radial position may establish an axial plane of reference relative to which successive readings and incremental radial positions may be compared. Precise axial advance of probe 27 is accomplished by rotation of adjusting knob 42 and worm 45 which gradually rotates a worm wheel 46 (not shown) and screw 32 which feeds nut 31, fixed to mobile casing 14 restrained against rotation by key screw 48, in order to effect gradual axial displacement. Compression spring 30 establishes a bias of nut 31 against threads of screw 32 to eliminate backlash in axial feed and retraction so that accuracy of probe 27 displacement may be gauged with an accuracy of 1/100 millimeter.

Upon manually advancing the probe through adjustment knob 42 to cornea contact, indicated by an audible signal, and registration of the axial position, the probe is retracted and adjusted incrementally to progressive radially outward positions, and manually advanced at each position to an audibly detected contact. Following each series of readings on a radial arc, head 25 may be rotated, typically 45°, for a new series of radial arc readings which can be repeated, typically at eight 45° increments, to provide a "map" of 80 corneal surface readings relative to the initial plane of reference from which an accuracy of corneal curvature can be calculated with unprecedented accuracy. The number and magnitude of radial and rotational adjustments, may of course be varied in accordance with the requirements for each individual patient.

With reference to the optical features of the apparatus, ocular 38 consists of a multiple 10 power lens unit which gives magnification to the observer of the area being studied. Such specific lens power may be varied according to the magnification desired. Objective lens 17 which may be a two lens system with an effective power in the order of 100 diopters or a single lens with a power in the order of 60 diopters provides focal length for the system and is mounted in the supporting lens holder cylinder 16 with provisions for adjustment of the ocular to provide the exact focus to any operator's eye which may have varying degrees of amotropia. Mounted in alignment with ocular 38 and objective lens 17, optical plastic beam splitter 12 reflects light 45° to front surface mirror 13 so that it will focus at a distance coordinated with objective lens 17. Fixation device 50 is mounted above beam splitter 12 for reflection by mirror 13 along the line of sight 52 corresponding with the axis of the apparatus.

A potentiometer 44, the example employed being of a design such as the HEDS-5000 series incremental optical encoder disclosed in Hewlett Packard's Technical Data of Jan. 19, 1985, transmits a digital signal to be counted. The proportionate ratio movement of shaft and encoder revolution to distance of mobile probe movement is one revolution to one millimeter of movement. The digital signal provided by the encoder is displaced by an LED counter in millimeters. The corresponding chord on the cornea is converted to dioptic slope value mathematically.

In conducting the examination, the eye of the patient is anesthesized to avoid any sensation from contact. A nominal voltage is all that is required to establish a potential which may be sensed to actuate the circuit for the audible signal.

It is of course optional for the examining eye care physician to determine the number and location of necessary readings from the potential of eighty or more positions which provides sufficient optional flexibility in number and area to meet any particular requirements such as may be involved in prescribing contact lenses covering a substantial area of the cornea. The slope of the cornea measured out to the limbus will also provide data for radial Keratotomy.

Figure 2:
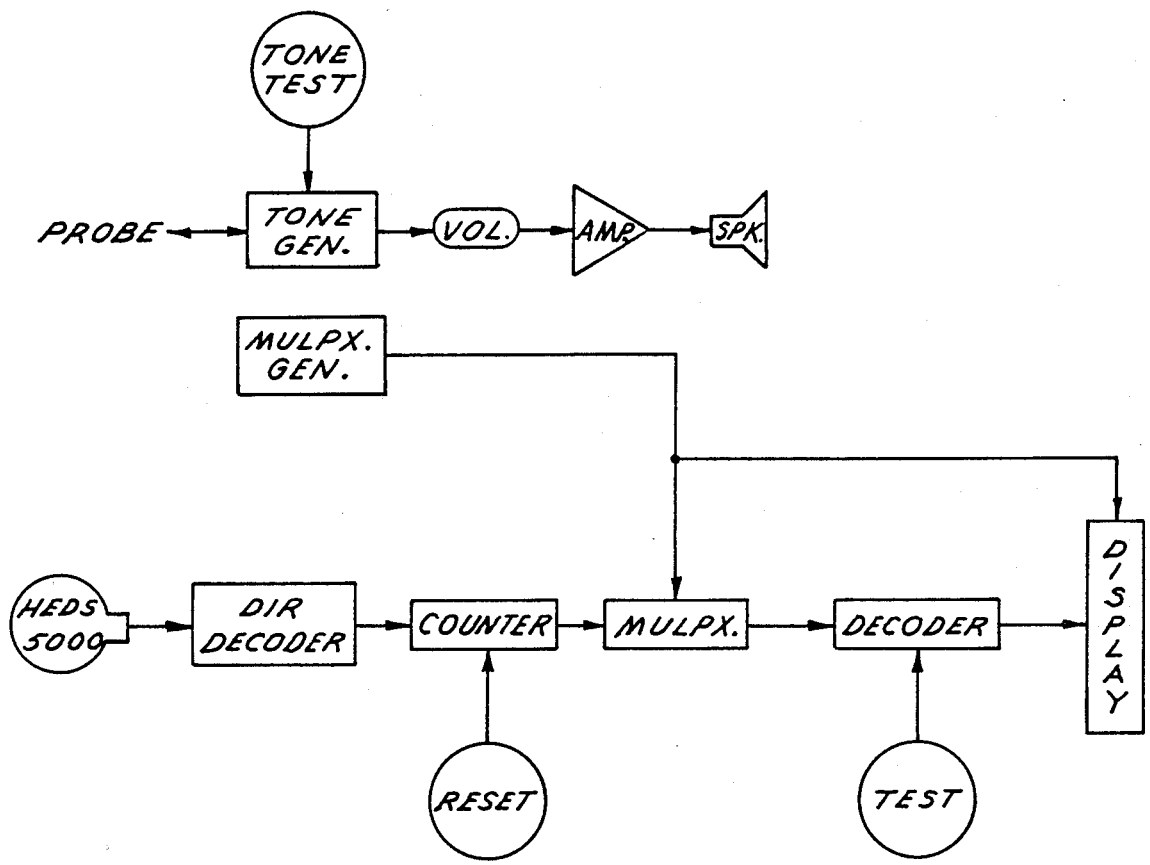
FIG. 2 is a schematic diagram of the electrical and electronic components employed in generating an audible contact tone and visual display of axial displacement measurements.
Figure 6:
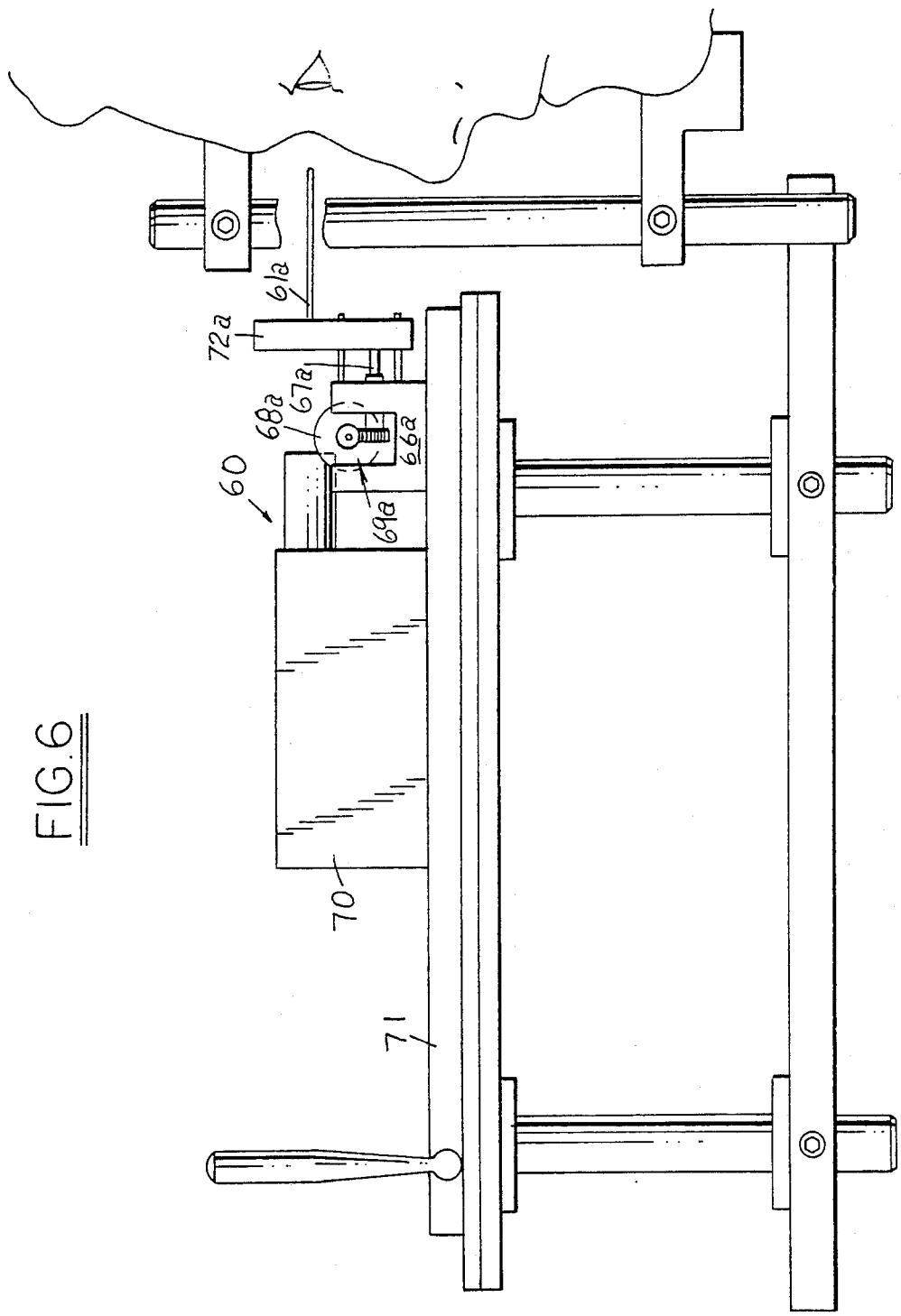
FIG. 6 is a side elevation of the apparatus mounted on an adjustable gimbal plate relative to the head of a patient.

With reference to FIG. 2, a schematic diagram indicates use of the electrical signal established by probe 27 to actuate a tone generator with volume control of amplification to a speaker audible to the operator. Likewise, a schematic diagram illustrates state of the art components employed in generating a display of incremental axial feed from the encoder 44.

With reference to FIGS. 3-6, the automated modification comprises closed circuit television monitor 60; probes and probe supports 61a and 61b; floating supports 62a and 62b controlled by stepper motor (not shown) along X-axis; remote cable connection 63 to stepper motor (not shown) for control of floating supports 62a and 62b; floating supports 64a and 64b controlled by stepper motor (not shown) along Y-axis; remote cable connection 65 to stepper motor (not shown) for control of floating supports 64a and 64b; relatively stationary support 66a for feed screw 67a turned by stepper motor 68a through reduction worm gearing 69a advancing floating support 72a and its associate probe support 61a along Z-axis, a duplicate of support 72a (not shown) being employed for advancing probe 61b; and camera mount 70 on adjustable gimbel mounting plate 71. Flexible cable servo-connections (not shown) from the X-axis drive 63 to corresponding floating support 62b provide simultaneous actuating from a single stepper motor; and likewise a servo-connection from remote cable connection 65 for the corresponding Y-axis floating support 64b provide for simultaneous Y-axis actuation.

X-Y-Z actuators schematically shown in FIGS. 3-6 are adaptations of the "state-of-the-art" controller commercially available under the tradename "A-BUS Smart Stepper Controller SC-149", relevant specifications for which are attached hereto as EXHIBIT A, pages 2-8 and 12 from the A-BUS commercial manual, Alpha Products Inc. of Darien, Connecticut.

In adapting the A-BUS system to the present application, each probe is operated independently along its Z-axis while a synchronizing gear box, and flexible cable coordinate the movement of respective probes 61a and 61b for the X-axis, and similarly for the Y-axis, so that a single stepper motor may accommodate simultaneous movement for both probes along each X and Y axis while a separate stepper motor is employed for each probe relative to the Z-axis. The latter is most critical in advancing the probe into physical contact with the cornea after pre-positioning in the respective X and Y axes. All four stepper motors are controlled by the Smart Stepper Motor Control SC-149 in conjunction with a computer which runs the program for selection of data points by instructions to the motor. The SC-149 reads back the position of the motors once the resistance circuit is completed between each probe touching the eye and the patient's chin in the chin rest. A current 0.00025 milliamps is passed through the patient in order to throw a "read" relay which is the limiting switch for the individual probes. The distance moved is then calculated from the known reference point and, as previously indicated, this distance from each probe is mathematically converted to an arc value, the arc being determined by the position of the X-axis setting of the respective probes. The settings can be from a range of 0 to 15+ millimeters from apex of the cornea depending on the practitioner's selection during initial patient profile programming phase (PPPP). This PPPP is completed by the practitioner prior to any measurements being made. The computer's prompt must be answered within the instrument's ranges for a complete set of data retrieval. Once entered, the computer program and the SC-149 completes the routine of selected data points requested, calculates the arc curve of each request, and is capable of averaging multiple arcs for additional empirical information. Information is printed out as raw data or placed in graphics.

A high impedance current sensor commercially available under the designation RCS3/88, will detect the resistance between probe and chin rest.

By pre-programming the data points to be checked for a given patient's cornea and employing two probes simultaneously for mapping each half of the eye, a complete reading can be taken, while constantly under TV surveillance by the practitioner, in a relatively brief time of examination as compared with the manual system of the first embodiment.

In a preferred embodiment, 120 potential data points, 60 on each side, are available in the program all of which are capable of being automatically read in a time range of 45 to 90 seconds. However, in a typical examination, two points at 5 and 10 mm spacing on each side of the apex in each of four arcs (16 points total) will suffice for accurate contact lens prescription, with proportionately shorter time required for the examination of each eye. Precision floating slides mounted on a solid base with appropriate stepper motors render the system practical in operation with great accuracy of measurement.

I claim:

1. Method for measuring corneal curvature comprising the steps of establishing fixed position of subject's eye for examination directed by visual focusing longitudinally toward a fixation point on a fixed solid apparatus base, moving an electrically conductive probe mounted on said base successively to a plurality of spaced predetermined positions relative to the corneal apex of the subject, moving said probe at each of said positions longitudinally to a point of sensing the corneal surface at said position, and recording the relative longitudinal differential dimensions of probe advancement to effectively map corneal curvature corresponding to said points over a predetermined corneal surface area.

2. The method of claim 1 including individual steps of manually adjusting radial and angular positions of said probe successively to predetermined positions relative to said apex.

3. The method of claim 2 including the step at each of said positions of advancing said probe longitudinally to make physical contact with the cornea of said subject.

4. The method of claim 3 including the step of electrically sensing the contact of said probe with said cornea.

5. The method of claim 4 including the employment of said electrical sensing for generating an audible signal.

6. The method of claim 3 including means for accurately measuring the longitudinally differential positions of said probe.

7. The method of claim 3 including means for accurately measuring the longitudinally differential positions of said probe by encoder means.

8. Method of claim 1 for measuring corneal curvature comprising, more specifically, the steps of preprogramming an initial patient profile programming phase to establish data points of a corneal surface to be checked, providing computer instructions for controlling probe means for touching the corneal surface at each of the required data points, employing the computer instructions to position said probe means along X, Y, and Z-axes to reach each data point on the corneal surface through precision stepper motors mounted on a fixed base relative to a headrest for the patient, positioning the patient's head in said headrest with the patient's eye in a fixed orientation, electrically sensing the contact of the probe with the corneal surface through a resistance circuit passing through the patient, sensing the instant of contact upon advancement of the probe first along X and Y, and finally Z-axes, recording the relative X, Y, and Z axes dimensions at each data point, and converting said dimensions to a corneal profile map of the patient's eye.

* * * * *

UNITED STATES PATENT AND TRADEMARK OFFICE
CERTIFICATE OF CORRECTION

PATENT NO. : 4,861,155
DATED : August 29, 1989
INVENTOR(S) : Max Downey

It is certified that error appears in the above—identified patent and that said Letters Patent is hereby corrected as shown below:

Column 2, line 49, "position" should read --positive--;

Column 4, line 20, "then" should read --ten--.

Signed and Sealed this

Twenty-fifth Day of December, 1990

Attest:

HARRY F. MANBECK, JR.

*Attesting Officer*     *Commissioner of Patents and Trademarks*